United States Patent [19]

Forsyth

[11] 4,196,990
[45] Apr. 8, 1980

[54] ADAPTER FOR COUPLING A PHOTOGRAPHIC CAMERA WITH A VIEWING DEVICE

[75] Inventor: Robert P. Forsyth, Carlisle, Mass.

[73] Assignee: Polaroid Corporation, Cambridge, Mass.

[21] Appl. No.: 14,692

[22] Filed: Feb. 23, 1979

[51] Int. Cl.² .................. A61B 1/04; G03B 29/00
[52] U.S. Cl. ........................... 354/62; 128/6; 352/131; 354/79
[58] Field of Search ............ 354/62, 79, 222; 352/131; 350/19; 128/4, 6, 8

[56] References Cited

U.S. PATENT DOCUMENTS

| | | | |
|---|---|---|---|
| 3,548,808 | 12/1970 | Takahashi | 128/6 |
| 3,556,085 | 1/1971 | Takahashi | 128/6 |
| 3,817,635 | 6/1974 | Kawahara | 356/171 |
| 3,900,021 | 8/1975 | Makepeace et al. | 128/4 |
| 3,994,288 | 11/1976 | Stumpf | 128/6 |
| 4,013,347 | 3/1977 | Nakamura | 350/188 |
| 4,036,218 | 7/1977 | Yamashita et al. | 128/4 |
| 4,157,216 | 6/1979 | Plummer | 354/62 |

OTHER PUBLICATIONS

Stanford, B., "Theoretical First Principles of Endoscopic Photograph," in *J. of Photo. Sc.*, vol. 3, 1955, pp. 1–4.

*Primary Examiner*—John Gonzales
*Attorney, Agent, or Firm*—Francis J. Caufield

[57] ABSTRACT

An adapter is provided by which an image formed by the eyepiece of an optical viewing device such as an endoscope can be simultaneously viewed and photographed with a motion picture camera of the type having a reflex viewing system which has an entrance pupil that occupies only a portion of the camera objective taking lens system and which is offset with respect to the optical axis of the camera objective taking lens system. The adapter operates to align the center of the viewing device exit pupil at a predetermined point along a line connecting the centers of the camera objective lens system and viewing system entrance pupils to preclude vignetting of the camera viewing system entrance pupil.

3 Claims, 6 Drawing Figures

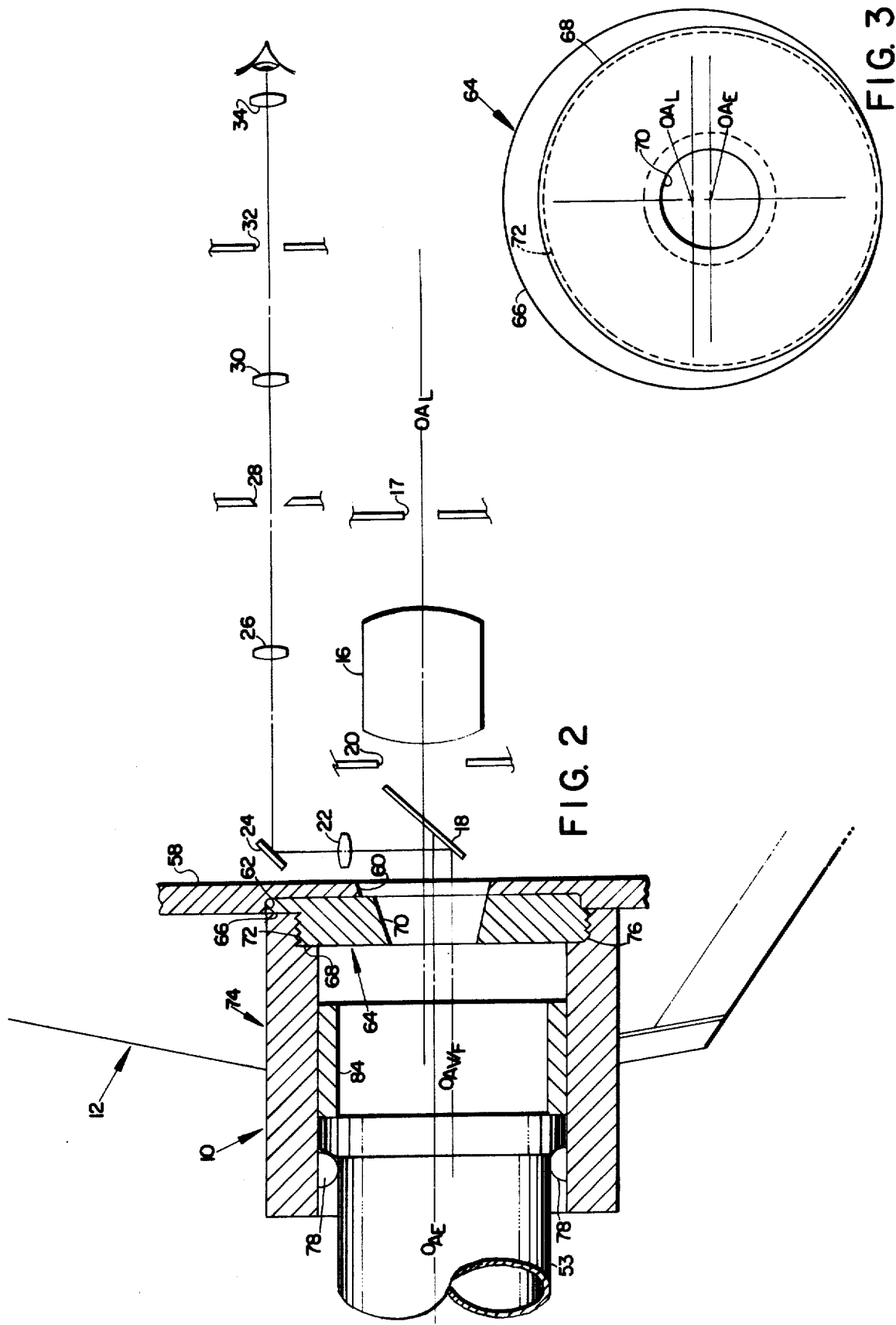

ADAPTER FOR COUPLING A PHOTOGRAPHIC CAMERA WITH A VIEWING DEVICE

BACKGROUND OF THE INVENTION

1. Field of the Invention

This invention in general relates to photographic apparatus and more specifically to an adapter by which a photographic motion picture camera can be coupled to an optical viewing device such as an endoscope to permit simultaneous viewing and photographing of the image formed by an eyepiece of the viewing device.

2. Description of the Prior Art

Endoscopes are optical viewing devices well known to the medical profession for their usefulness in diagnosing disease. With an endoscope, a physician, typically a surgical consultant, visually examines the interior of a patient's body organs for pathological processes whose presence is suspected or indicated by clinical and laboratory findings.

Once detected, a pathology is then carefully studied to determine its precise nature and extent so that the proper course of treatment can be decided upon and recommended to the patient.

For a variety of reasons, it is often advantageous for the surgical consultant to have a permanent photographic record of the endoscopic findings. For example, such records are useful for educational purposes. Also, they can form part of the patient's permanent medical record or can be used as a basis for evaluating changes in the pathology. Additionally, endoscopic photographs serve as a powerful tool for promoting communication between the examining physician and others involved or interested in the diagnosis and as a means for informing the patient about the nature of his illness.

Although endoscopic photographs have their beneficial uses, they are somewhat difficult to obtain because the clinical form of most endoscopes generally is unsuitable for photography, because of the requirements of medically sound and safe practice, and because of the overriding concern for patient safety and comfort.

Photographic and optical principles, for instance, demand that any camera chosen for use with an endoscope must be able to be focused on the image provided by the endoscope's eyepiece, that adequate lighting be provided to assure acceptably exposed photographs, and that the examining physician, and sometimes more than one, be able to see an image of the field in examination immediately before and after a picture is taken in case of stills and continuously in the case of motion pictures. And all of this must be accomplished by apparatus which ideally shares the endoscope's single optical path.

Sound clinical procedure, on the other hand, imposes certain design constraints which makes it difficult to satisfy the photographic and optical requirements of endoscopic apparatus. One major obstacle, for example, is the clinical desirability of using only one endoscope for both the visual clinical examination and the photographic work. It is neither convenient for the examining physician nor fair to the patient to have to withdraw the clinical endoscope once a pathology has been located, insert the photographic endoscope, photograph the field of interest, withdraw the photographic endoscope and reinsert the clinical endoscope. A process like this would obviously complicate an endoscopic examination by adding additional risk and discomfort to what inherently can be an uncomfortable ordeal. Also, since the endoscope must be manipulated quite a bit throughout the examination, any photographic apparatus designed for use with the clinical endoscope should not hamper the physician's freedom of movement or require extensive operations involving attachment and detachment of the photographic apparatus with the endoscope.

Consequently, apparatus used for endoscopic photography must be easy to use, i.e. manipulate, must not unduly prolong the endoscopic examination, ideally, should be mechanically and optically compatible with an existing form of clinical endoscope and, as well, must be capable of reliably producing photographs which are acceptably exposed while containing adequate detail.

Finally, such apparatus must be absolutely safe and must, in particular, be free from any danger of causing electrical shock or creating unduly high temperatures which may come into contact with the patient.

Given the above general considerations, it is evident that the problems associated with providing apparatus for use in endoscopic photography are varied—involving both technical and humane considerations. In the past, these problems have been dealt with in a variety of ways by providing either specially designed photographic systems whose use is limited to endoscopic photography or by providing adapters by which existing cameras can be used with an existing endoscope. For examples reference may be had to U.S. Pat. No. 3,368,643 issued to John E. Hotchkiss on Feb. 1, 1972 and entitled "Endoscope For Photographic Recording"; U.S. Pat. No. 3,918,072 issued to Toshihiro Imai et. al. on Nov. 4, 1975 and entitled "Single-Lens Reflex Optical System For An Endoscope"; U.S. Pat. No. 3,995,287 issued to Karl Storz on Nov. 30, 1976 and entitled "Endoscopic Camera"; U.S. Pat. No. 3,900,021 issued to Anthony Peter Walter Makepeace et. al. on Aug. 19, 1975 and entitled "Coupling for Endoscopes And Instruments Particularly Camera"; U.S. Pat. No. 3,994,288 issued to Joseph G. Stumpf on Nov. 30, 1976 and entitled "Colposcope", and an Article by Brian Stanford which appears in *The Journal of Photographic Science*, volume 3, 1955, and is entitled "Theoretical First Principles of Endoscopic Photography".

However, none of the foregoing publications appear to deal directly with the specific problem with which the present invention is concerned. In particular, the primary object of the present invention is to provide an adapter by which a motion picture camera of the type having a reflex viewing system which has an entrance pupil that occupies only a portion of the entrance pupil of the camera taking lens and has a central axis which is laterally offset with respect to the optical axis of the camera taking lens can be joined to the proximal end of an optical viewing device such as an endoscope so that the image of an object formed by the viewing device can be viewed and photographed simultaneously wherein the viewing device is of the type which has an eyepiece located at its proximal end for forming a collimated to nearly collimated object image which is visible through an exit pupil spaced behind the eyepiece and subtends an angular field at the exit pupil which is smaller than the angular field of view of the camera taking lens and viewing system.

Although none of the aforementioned publications appear to provide apparatus by which the primary object of the present invention can be accomplished, there is described in U.S. patent application Ser. No. 918,779, filed on June 26, 1978 in the name of William T. Plummer and entitled "An Adapter For Optically Coupling A Photographic Camera With A Viewing Device", now U.S. Pat. No. 4,157,216, an adapter which does accomplish the primary object of the present invention. However, the Plummer adapter utilizes a lens system in combination with a light diffusing element to spread to optical viewing device exit pupil so that its size matches that of the camera taking lens entrance pupil and to improve the uniformity of illumination over the camera taking and viewing system. Although the Plummer adapter is satisfactory, it is relatively expensive and complex. Therefore, there exists a need for a simplified, inexpensive adapter for accomplishing the primary object of the present invention.

Other objects of the invention will in part be obvious and will in part appear hereinafter. The invention accordingly comprises the apparatus possessing the construction, combination of elements, and arrangement of parts which are exemplified in the following detailed disclosure.

SUMMARY OF THE INVENTION

This invention in general relates to photographic apparatus and more specifically to an adapter for use with a photographic camera to join the camera to the proximal end of an optical viewing device such as an endoscope so that the image of an object formed by the viewing device can be viewed and photographed simultaneously.

The camera is of the type which has a photographic objective lens focused at infinity and a reflex viewing system which has an entrance pupil that occupies only a portion of the entrance pupil of the camera taking lens and has a central axis which is laterally offset with respect to the optical axis of the camera taking lens, and the viewing device is of the type which has an eyepiece located at its proximal end for forming a collimated or nearly collimated object image which is visible through an exit pupil spaced behind the eyepiece wherein the angular field of the object image formed by the eyepiece at the exit pupil is smaller than the angular field of view of the camera taking lens and viewing system.

The adapter of the invention comprises a coupling for positioning the viewing device in light tight relation to the camera. The coupling has one end adapted for attachment to the camera and another end which has a central axis and which is adapted to releasably receive and position the viewing device eyepiece so that the optical axis of the viewing device exit pupil is collinear with the central axis of the other end. The coupling is further configured and arranged so that, when the viewing device eyepiece is connected with the coupling other end and the coupling one end is attached to the camera, the optical axis of the viewing device exit pupil is always aligned at a predetermined point along a line passing through the center of the camera taking lens and viewing system entrance pupils.

Structured in the foregoing manner the coupling operates to preclude vignetting of the camera viewing system entrance pupil by aligning the optical axis of the viewing device exit pupil closer to the central axis of the camera viewing system entrance pupil thereby making more image forming light from the viewing device eyepiece available for entrance into the camera viewing system than would otherwise enter the camera viewing system absent the coupling.

DESCRIPTION OF THE DRAWINGS

The novel features that are considered characteristic of the invention are set forth with particularity in the appended claims. The invention itself, however, both as to its organization and method of operation together with other objects and advantages thereof will best be understood from the following description of the illustrated embodiment when read in connection with the accompanying drawings wherein like numbers have been employed in the different figures to denote the same parts and wherein:

FIG. 2 is a vertical section of a portion of the camera of FIG. 1, taken generally along line 2—2 of FIG. 1, shown in combination with a portion of the endoscope of FIG. 1;

FIG. 3 is a front elevational view of a portion of the adapter of the invention;

DESCRIPTION OF THE PREFERRED EMBODIMENT

Figure 1:
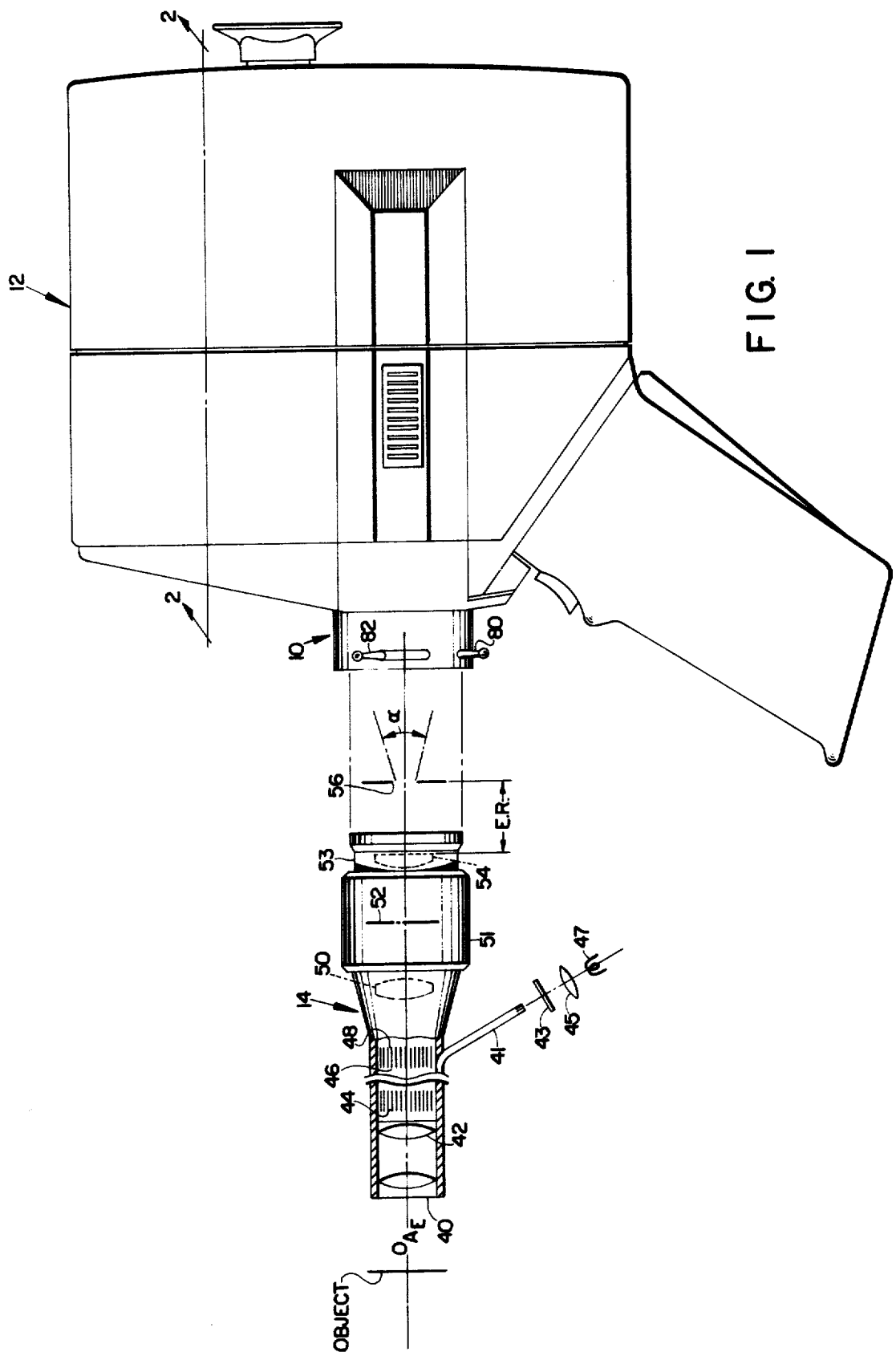
FIG. 1 is a side-elevational view of a movie camera in which the adapter of the invention is incorporated shown with an endoscope which is partially sectioned.

Referring now to FIG. 1, there is shown a motion picture camera 12 in which the adapter of the invention, which is designated at 10, is incorporated for the purpose of joining the camera 12 to the proximal end of an optical viewing device in the form of an endoscope 14 so that an object image formed by the optical viewing device 14 can be viewed and photographed simultaneously via the optical system of the camera 12.

The motion picture camera 12 may be any of a number of well-known types but, as illustrated, represents a modified version (no zoom lens) of Polaroid Corporation's Polavision camera which is adapted in a well-known manner to accept instant color motion picture film that can be processed and viewed via a player (not shown) immediately after it has been exposed.

As seen in FIG. 2, the camera 12 includes an fl.8, objective taking lens, designated schematically at 16, for forming an image of a photographic scene in a focal plane immediately behind an exposure gate 17. The film is advanced in the focal plane past the exposure gate 17 for exposure in a well-known manner. The objective taking lens 16 is set for infinity focus and in combination with the peripheral edges of the exposure gate 17 defines the field of view for the camera 12. Located forward of the objective taking lens 16 is an aperture 20 which serves as the stop for the camera objective taking system.

Also provided in the camera 12 is a well-known reflex viewing system which comprises a beamsplitter 18 which is located forward of the camera aperture stop 20. The beamsplitter 18 operates in a well-known manner to intercept image forming rays from a scene and direct them along a folded optical path toward an objective lens 22 which functions as a relay. The optical path of the viewing system is then again folded by a mirror 24 which directs light toward an erector lens 26. Located behind the erector lens 26 is an aperture stop 28 which is followed by a second erector lens 30 and afterwards by a field stop 32. Behind the field stop 32 is located an eyelens 34 which may be adjusted to provide the photographer with a view of an image of the scene formed by the preceding elements of the viewing system.

As shown in FIG. 2, the various elements which comprise the camera viewing system are structured and arranged with respect to one another and the camera objective taking lens 16 so that the optical axis, $OA_{VF}$, of the camera viewing system, as it emerges from the camera 12, is offset by a predetermined distance below the optical axis, $OA_L$, of the camera objective taking lens 16.

Figure 4:
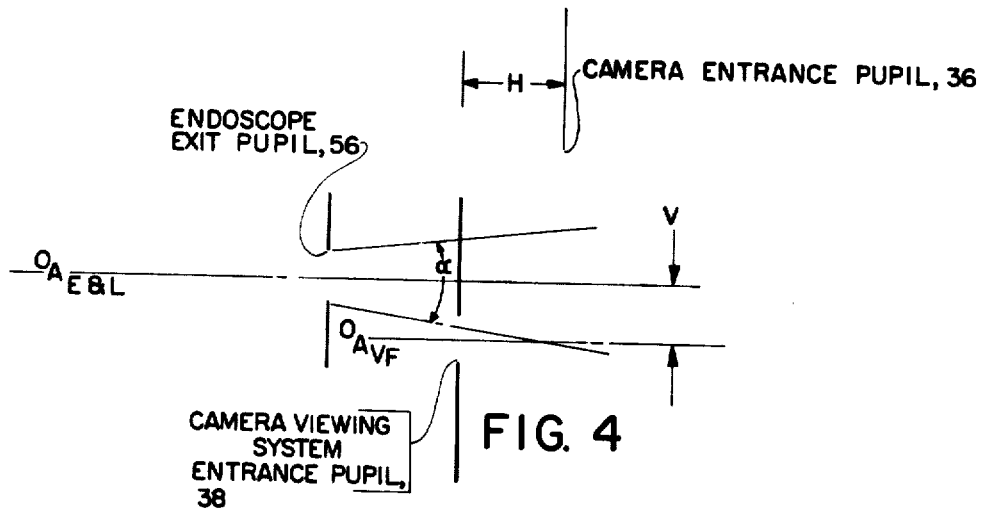
FIG. 4 is a diagrammatic side elevational view which shows the pupil locations of the endoscope and camera of FIG. 1 without the adapter of the invention.
Figure 5:
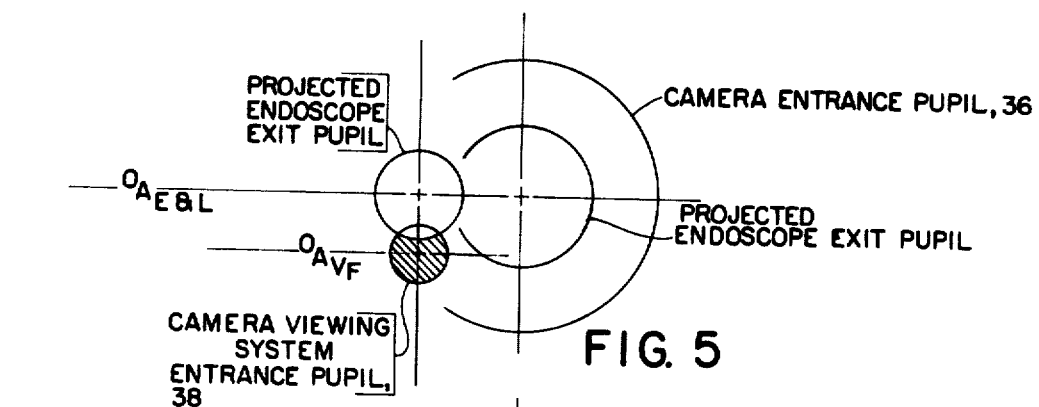
FIG. 5 is a diagrammatic view derived from taking sections normal to the paper in FIG. 4 and shows the exit pupil of the endoscope of FIG. 1 projected onto the entrance pupils of the camera of FIG. 1.

The foregoing arrangement of the camera taking and viewing systems causes the center of their respective entrance pupils, i.e., the images of their respective aperture stops 20 and 28 as seen looking into the camera 10, to be laterally offset with respect to one another as shown at 36 and 38 respectively in FIGS. 4 and 5. The entrance pupils, 36 and 38, of the camera taking and viewing systems are also separated axially by a distance, H, as well as laterally by a distance, V, as best seen in FIG. 4. The axial and lateral separation between the entrance pupils, 36 and 38, of the camera taking and viewing systems results in a parallax view of the scene between the two camera optical systems. This parallax between the two camera optical systems, a not uncommon occurrence, is not a serious problem in normal picture taking applications—say at object distances beyond five feet—but, for reasons which will become apparent, must be taken into account when the camera 12 is used with the endoscope 14.

The endoscope 14 constitutes an optical viewing device of the type by which an image (usually magnified) of a distant object can be observed through a small diameter viewing pupil which is located away from the object by a distance at least equal to several viewing pupil diameters. As best shown in FIG. 1, the endoscope 14 comprises an objective lens consisting of a pair of spaced apart doublets 40 and 42, respectively, which, in combination form a real image of an object on a distal end 44 of an elongated film optic bundle 46. The real image formed on the fiber optic bundle distal end 44 is transferred in a well-known manner via the fiber optic bundle 46 to a proximal end 48 thereof.

An objective lens 50 forms a real inverted image (usually magnified) of the fiber optic bundle proximal end 48 in a focal plane 52 that is spaced behind the objective lens 50. In an eyepiece 53, there is located an eyelens 54, adjustable in a well-known manner by a rotatable collar 51, for re-imaging the image formed in the focal plane 52 so that it can be comfortably viewed through an exit pupil 56 which is spaced behind the eyelens 54 by a distance, E.R. The distance E.R. is referred to as the eye relief because the eye must be placed at the exit pupil 56 to see the full field of view of the endoscope 14.

In practice, the eye is placed at or near the endoscope exit pupil 56 and the eyepiece 53 is adjusted by rotating collar 51 until the image seen is sharp. When this is done, a collimated to nearly collimated object image is formed which allows the eye to be relaxed while viewing it. The object image thus formed subtends a solid angle, $\alpha$, about the endoscope optical axis, $OA_E$, at the endoscope exit pupil 56, and the angle, $\alpha$, is substantially smaller than the angular field of view of the camera viewing and taking systems.

The object is illuminated via another fiber optic bundle 41 which receives light at its proximal end from a lamp 47, condenser lens 45 and a heat absorbing filter 43 which cools the light thereby keeping it at a comfortable temperature.

In order to use the camera 12 to simultaneously view and photograph the image available at the endoscope exit pupil 56, it is necessary to join the camera 12 to the endoscope eyepiece 53 so that all of the rays emerging from the endoscope exit pupil 56 within the solid angle, $\alpha$, enter both the camera entrance pupils 36 and 38. If this condition is not satisfied, vignetting and/or a loss of image can occur which prohibits simultaneous viewing and photographing of the endoscope object image.

Ideally, the foregoing condition is satisfied by placing the camera entrance pupils 36 and 38 exactly on the endoscope exit pupil 56. However, this is not possible for two reasons. The first is that the entrance pupil locations are inside the camera 12 and are axially recessed by a distance which physically makes it impossible to place them on the endoscope exit pupil 56, and the second is that the entrance pupils 36 and 38 are laterally and horizontally offset with respect to one another as previously described. Consequently, the exit pupil 56 must be located forward of the entrance pupils 36 and 38.

Referring now to FIG. 4, it can be seen that if the endoscope optical axis, $OA_E$, is made coincident with the objective lens optical axis, $OA_L$, part of the cone of illumination from the endoscope exit pupil 56 does not enter the viewing system entrance pupil 38. The result is illustrated in FIG. 5 which shows the endoscope exit pupil 56 projected onto the camera entrance pupils 36 and 38 in planes at the entrance pupil locations. The cross-hatched area of the entrance pupil 38 represents the amount of reduction or vignetting of the entrance pupil 38 clear aperture and the overlapping of the projected endoscope exit pupil 56 with the viewing system entrance pupil 38 represents the size of the aperture through which the image at the exit pupil 56 can be seen. It is clear from this illustration that the image seen through the camera viewing system is substantially darker than that seen by the film through the taking lens entrance pupil 36 where there is no vignetting. Thus, this alignment arrangement prohibits viewing the image while simultaneously photographing it.

The present invention solves this vignetting problem in a manner which will best be understood by now referring to FIGS. 2 and 3 wherein it can be seen that the adapter 10 comprises a coupling formed of a connector plate 64 and a cylindrical tubular section 74.

The connector plate 64 includes a rear circular section 66 which fits into a complementary configured circular recess 62 which is located in a camera structural wall 58. The rear circular section 66 is concentric about the objective lens optical axis, $OA_L$. The circular recess 62 provides the mount for a zoom lens section (not shown) which was removed for replacement by the present adapter 10. Located in the circular recess 62 is a centrally disposed light admitting aperture 60.

The rear circular section 66 is preferably fixedly attached to the structural wall 58 and this can be accomplished in any well-known manner.

Located ahead of the rear circular section 66 is a front circular section 68 which is eccentric with respect to the rear circular section 66. Both the front and rear circular sections, 66 and 68, have a diverging aperture 70 therethrough which is structured to pass all of the light emerging from the viewing device exit pupil 56 toward the camera entrance pupils 36 and 38. The central axis of the aperture 70 is concentric with the front circular section 68 (FIG. 3) and is offset and parallel with respect to the camera objective taking lens optical axis, $OA_L$. The amount of offset is chosen so that the central axis of the aperture 70 always lies along a line connecting the centers of the camera entrance pupils, 36 and 38.

The circumferential surface of the front circular section 68 is provided with threads 72 which fit a complementary threaded section 76 of the tubular section 74 to join the circular tubular section 74 and the connector plate 64 so that they are concentric.

The forward end of the tubular section 74 is provided with well-known means for releasably receiving and centrally locating therein the endoscope eyepiece 53. The releasing and locating means comprise a series of balls 78 which can be retracted into the tubular section front end by rotating a lever 82 with respect to a stationary lever 80 (see FIG. 1). With the balls 78 retracted, the endoscope eyepiece 53 slides into the tubular section 74 until it is stopped by a locating sleeve 84. The locating sleeve 84 is axially adjustable to establish the gap between its forward surface and the balls 78. Once the eyepiece 53 is slid into the tubular section 74, the lever 82 is released to lower the balls 78 in place to grip the eyepiece 53. When this happens, the endoscope optical axis, $OA_E$, is always automatically aligned along a predetermined point along a line connecting the centers of the camera entrance pupils 36 and 38.

Figure 6:
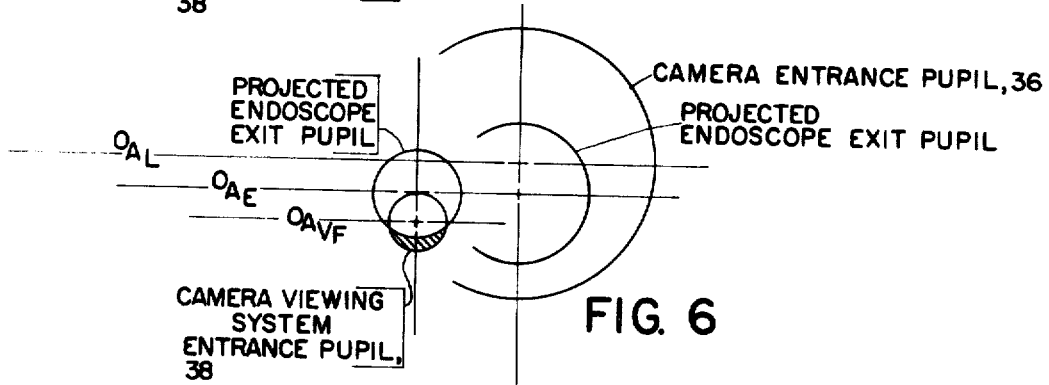
FIG. 6 is similar to FIG. 5 but shows the exit pupil of the endoscope of FIG. 1 projected onto the camera entrance pupils with the adapter of the invention.

FIG. 6 illustrates how the adapter 10 aligns the endoscope exit pupil 56 with respect to the camera entrance pupils 36 and 38 and how it it operates to preclude vignetting of the camera viewing system entrance pupil 38. The adapter 10 aligns the optical axis of the endoscope exit pupil, $OA_E$, closer to the central axis, $OA_{VF}$, of the camera viewing system entrance pupil 38 thereby making more image forming light from the endoscope exit pupil 56 available for entrance into the camera viewing system than would otherwise enter it absent the adapter 10. The improvement which results from the adapter 10 of the invention can be appreciated by comparing the reduced cross-hatched area and increased overlap areas of the projection of the exit pupil 56 onto the entrance pupil 38 of FIG. 6 with those of FIG. 5. It is clear from the comparison that the adapter 10 reduces the amount of vignetting and increases the aperture through which the endoscope object image can be observed. Also, there is no loss of light entering the camera taking entrance pupil 36 as can also be seen from FIG. 6.

Structured in the foregoing manner, the adapter 10 provides a light-tight connection between the endoscope 14 and the camera 12 and operates to preclude vignetting of the camera viewing system so that the image formed by the endoscope 14 can be viewed and photographed simultaneously with the camera 12.

Certain changes may be made in the above described embodiment without departing from the scope of the invention, and those skilled in the art may make still other changes according to the teachings of the disclosure. Therefore, it is intended that all matter contained in the above description or shown in the accompanying drawings shall be interpreted as illustrative and not in a limiting sense.

What is claimed is:

1. An adapter for use with a photographic camera to join the camera to the proximal end of an optical viewing device such as an endoscope so that the image of an object formed by the viewing device can be viewed and photographed simultaneously wherein the camera is of the type which has a photographic objective lens focused at infinity and a reflex viewing system which has an entrance pupil that occupies only a portion of the entrance pupil of the camera taking lens and has a central axis which is laterally offset with respect to the optical axis of the camera taking lens and wherein the viewing device is of the type which has an eyepiece located at its proximal end for forming a collimated to nearly collimated object image which is visible through an exit pupil spaced behind the eyepiece wherein the angular field of the object image formed by the eyepiece at the exit pupil is smaller than the angular field of view of the camera taking lens and viewing system, said adapter comprising:

a coupling for positioning the viewing device in light-tight relation to the camera, said coupling having one end adapted for attachment to the camera and another end which has a central axis and which is adapted to releasably receive and position the viewing device eyepiece so that the optical axis of the viewing device exit pupil is collinear with said central axis of said other end, and further configured and arranged so that, when said viewing device eyepiece is connected with said coupling other end and said coupling one end is attached to the camera, the optical axis of the viewing device exit pupil is always aligned at a predetermined point along a line passing through the center of the camera taking lens and viewing system entrance pupils, said coupling structured in the foregoing manner operating to preclude vignetting of the camera viewing system entrance pupil by aligning the optical axis of the viewing device exit pupil closer to the central axis of the camera viewing system entrance pupil thereby making more image forming light from the viewing device eyepiece available for entrance into the camera viewing system than would otherwise enter the camera viewing system absent said coupling.

2. The adapter of claim 1 wherein said one end of said coupling is adapted to be fixedly attached to the camera.

3. The adapter of claim 1 wherein said coupling comprises:

(a) a connector plate including a first circular section of given thickness and diameter and a second circular section, also of given thickness and diameter, located forwardly of said first circular section and eccentric with respect thereto, both said first and second circular sections having an aperture therethrough which is structured to pass all of the light emerging from the viewing device exit pupil toward the camera taking lens and viewing system entrance pupils and having a central axis with which said second circular section section is concentric and which is offset and parallel with respect to the optical axis of the camera taking lens and passes through said predetermined point; and (b) a cylindrical tubular shaped section having one end attached to said connector plate second circular section and concentric therewith and another end which includes said means for releasably receiving and centrally locating the viewing device eyepiece therewith.

* * * * *